United States Patent [19]

Plank et al.

[11] 4,011,278
[45] Mar. 8, 1977

[54] CONVERSION OF POLAR COMPOUNDS USING A ZSM-5 ZEOLITE CATALYST

[75] Inventors: Charles J. Plank, Woodbury; Edward J. Rosinski, Pedricktown; George T. Kerr, Trenton, all of N.J.

[73] Assignee: Mobil Oil Corporation, New York, N.Y.

[22] Filed: Feb. 3, 1975

[21] Appl. No.: 546,863

Related U.S. Application Data

[63] Continuation of Ser. No. 296,370, Oct. 5, 1972, abandoned, which is a continuation-in-part of Ser. No. 821,980, May 5, 1969, abandoned, which is a continuation-in-part of Ser. No. 494,846, Oct. 11, 1965, Pat. No. 3,442,795, which is a continuation-in-part of Ser. No. 261,494, Feb. 27, 1963, abandoned.

[52] U.S. Cl. .............................. 260/682; 260/668 R
[51] Int. Cl.$^2$ .......................................... C07C 1/24
[58] Field of Search ...................... 260/668 R, 682

[56] References Cited

UNITED STATES PATENTS

| | | | |
|---|---|---|---|
| 3,894,103 | 7/1975 | Chang et al. | 260/668 |
| 3,894,104 | 7/1975 | Chang et al. | 260/668 |
| 3,894,106 | 7/1975 | Chang et al. | 260/668 |
| 3,894,107 | 7/1975 | Butter et al. | 260/668 |
| 3,907,915 | 9/1975 | Chang et al. | 260/668 |

*Primary Examiner* — C. Davis
*Attorney, Agent, or Firm* — C. A. Huggett; M. G. Gilman

[57] ABSTRACT

Conversion, e.g. dehydration, of aliphatic organic oxygenates having up to about 6 carbon atoms by contact with a crystalline aluminosilicate zeolite, preferably ZSM-5, having a silica to alumina ratio substantially greater than 10, at a temperature of about 70° to 1400° F, depending upon the exact nature of the reactant and product.

2 Claims, No Drawings

CONVERSION OF POLAR COMPOUNDS USING A ZSM-5 ZEOLITE CATALYST

This application is a continuation of application Ser. No. 296,370, filed Oct. 5, 1972, now abandoned, which is a continuation-in-part of application Ser. No. 821,980, filed May 5, 1969, now abandoned, which is in turn a continuation-in-part of application Ser. No. 494,846 filed Oct. 11, 1965, now U.S. Pat. No. 3,442,795 which is a continuation-in-part of application Ser. No. 261,494 filed Feb. 27, 1963, now abandoned.

This invention relates to a proces of converting organic polar compounds. It more particularly refers to the conversion of aliphatic oxygenates using a special zeolite.

Zeolite materials, both natural and synthetic, have been demonstrated in the past to have catalytic capabilities for various types of hydrocarbon conversion. Certain zeolite materials are ordered crystalline aluminosilicates having a definite crystalline structure within which there are a large number of small cavaties which are interconnected by a number of still smaller holes or channels. These cavaties and channels are uniform in size. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves include a wide variety of positive ion-containing crystalline aluminosilicates, both natural and synthetic. These aluminosilicates can be described as a rigid three-dimensional network of $SiO_4$ and $AlO_4$ tetrahedra in which the tetrahedra are cross-linked by the sharing of oxygen atoms whereby the ratio of the total aluminum and silicon atoms to oxygen atoms is 1:2. The electrovalence of the tetrahedra containing aluminum is balanced by the inclusion in the crystal of a cation, for example, an alkali metal or an alkaline earth metal cation. This equilibrium can be expressed by formula wherein the ratio of $Al_2$ to the number of the various cations, such as Ca, Sr, $Na_2$ or $Li_2$, is equal to unity. One cation may be exchanged either in entirety or partially by another cation utilizing ion exchange techniques. By means of such cation exchange, it is possible to vary the size of the pores in the given aluminosilicate by suitable selection of the particular cation. The spaces between the tetrahedra are occupied by molecules of water prior to dehydration. The parent zeolite is dehydrated to activate it for use as a catalyst.

A description of such zeolites is found in U.S. Pat. Nos. 2,882,243, 2,971,824, 3,033,778 and 3,130,007, whose disclosures are hereby incorporated herein by reference.

In said copending application Ser. No. 494,846, it is pointed out that highly siliceous catalysts, that is zeolites with a high silica to alumina ratio, find extensive utility for transforming organic compounds which are catalytically convertible in the presence of acidic catalyst sites into modified organics. It is pointed out that the catalysts in question are exceptionally stable in a variety of enumerated processes which may be carried out at temperatures ranging from ambient temperatures of 70° F up to 1400° F., including processes in which the catalyst is periodically regenerated by burning off combustible deposits.

Among the organic conversion reactions mentioned in said copending application Ser. No. 494,846 are a number of reactions involving the conversion of polar organic compounds such, for example, as the dehydration of alcohols, alkylation of phenols, oxidation of alcohols and ketones, acids and the like, desulfurization of hydrocarbons, hydrogenation of alcohols, ketones and acids and the production of caprolactam from caprolactone and ammonia. Such copending application also discloses a number of reactions involving the formation of polar organic compounds as reaction products such, for example, as organic oxides from the oxidation of hydrocarbons including specifically the formation of ethylene oxide, propylene oxide, cyclohexanone, cyclohexanol and adipic acid, and the production of vinyl chlorides.

It is, therefore, an object of this invention to provide a novel process for converting organic polar compounds.

It is another object of this invention to provide an improved process for converting aliphatic organic polar compounds.

It is a further object of this invention to provide novel means for converting oxygenated aliphatic organic compounds.

Other and additional objects of this invention will become apparent from a consideration of this entire specification including the claims hereof.

In accord with and fulfilling these objects, one aspect of this invention resides in the conversion of polar organic compounds, especially lower aliphatic organic oxygenated compounds having up to about 6 carbon atoms therein, by contacting such with a crystalline aluminosilicate zeolite, preferably a ZSM-5 zeolite, having a silica to alumina ratio substantially greater than 10, at about 70° to 1400° F. Of particular importance is the dehydration of aliphatic organic oxygenates using this process and this catalyst. Specific class of oxygenated organic compounds suited to use in this invention are acetals, ketals, acid halides, alcohols, carboxylic acids, aldehydes, acid anhydrides. epoxides, ethers, esters, hemi acetals, gen diols, hydroxy acids, ketones, ketems, lactones, peracids, peroxides and sugars. Of particular importance are those oxygenates which contain more than two hydrogen constituents per oxygen constituent. Most preferred are those oxygenates which contain at least two hydrogens per oxygen and at least one hydrogen per carbon. The preferred oxygenates contain only carbon, oxygen and hydrogen. Of all the reactant compounds types and varieties set forth above, the alcohols, ethers and esters conforming to the atom ratios specified above are most preferred.

Representative specific oxygenated organic compounds useful in this invention include dimethyl ketal, acetyl chloride acetyl bromide, acetic acid, ethanol, ethylene glycol, acetaldehyde, succinic anhydride, acetic anhydride, succinic acid, ethylene oxide, cyclohexeneoxide, n-propyl ether, tetra hydrofuran, ethyl acetate, diethylmalonate, proprionaldehyde ethyl hemiacetal, p-dioxane, furan, 2-trichloro,-1,1 dihydroxy ethane, 1,3 bis(trifluoro),2,2 propaline glycol, glycolic acid, acetone, methyl ethyl ketone, ketene, dimethyl ketene, e-caprolactone, ethylorthoformate, peracetic acid, acetylperoxide and hexoze.

As was noted above, a key to the practice of this invention is believed to be the silica to alumina ratio of the zeolite catalyst. Ratios of greater than 10 have been noted to be useful. Preferably the silica to alumina ratio is up to about 200. Best results are obtained with the use of molecular sieves having a silica to alumina ratio of up to about 75.

The preferred crystalline aluminosilicate usable in the process of the present invention has been designated ZSM-5. Catalyst ZSM-5 is a crystalline aluminosilicate having the composition, expressed in mole ratios of oxides, as follows:

$$0.9 \pm 0.2\ M_{2/n}O:Al_2O_3:wSiO_2:yH_2O$$

wherein M is at least one cation and $n$ is its valence, $w$ is 5–100 and $y$ is from 0–40.

Members of the family of ZSM-5 zeolites possess a definite distinguishing crystalline structure whose X-ray diffraction pattern shows the following significant lines:

TABLE B

| Interplanar Spacing d (A) | Relative Intensity |
|---|---|
| 11.1 ± 0.3 | S |
| 10.0 ± 0.3 | S |
| 7.4 ± 0.2 | W |
| 7.1 ± 0.2 | W |
| 6.3 ± 0.2 | W |
| 6.04 ± 0.2 | W |
| 5.97 ± 0.2 | W |
| 5.69 ± 0.1 | W |
| 5.56 ± 0.1 | W |
| 5.01 ± 0.1 | W |
| 4.60 ± 0.1 | W |
| 4.35 ± 0.1 | W |
| 4.25 ± 0.1 | W |
| 3.85 ± 0.1 | VS |
| 3.75 ± 0.05 | S |
| 3.71 ± 0.05 | S |
| 3.64 ± 0.05 | M |
| 3.04 ± 0.05 | W |
| 2.99 ± 0.05 | W |
| 2.94 ± 0.05 | W |

The above were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 $I/I_o$, where $I_o$ is the intensity of the strongest line or peak, and $d$ (obs.), the interplanar spacing in A, corresponding to the recorded lines, were calculated. In Table A the relative intensities are given in terms of the symbols S=strong, M=medium, MS=medium strong, MW=medium weak and VS=very strong. It should be understood that this X-ray diffraction pattern is characteristic of all the species of ZSM-5 compositions. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

ZSM-5 zeolites can be used either in the alkali metal form, e.g., the sodium form, the ammonium form, the hydrogen form, or another univalent or multivalent cationic form. Preferably, one or other of the last two forms is employed. They can also be used in intimate combination with a hydrogenating component such as tungsten, vanadium, molybdenum, rhenium, nickel, cobalt, chromium, manganese, or a noble metal such as platinum or palladium where a hydrogenation dehydrogenation function is to be performed. Such component can be exchanged into the composition, impregnated therein or physically intimately admixed therewith. Such component can be impregnated in or on to ZSM-5, such as, for example, by, in the case of platinum, treating the zeolite with a platinum metal-containing ion. Thus, suitable platinum compounds include chloroplatinic acid, platinous chloride and various compounds containing the platinum amine complex.

The compounds of the useful platinum or other metals can be divided into compounds in which the metal is present in the cation of the compound and compounds in which it is present in the anion of the compound. Both types of compounds which contain the metal in the ionic state can be used. A solution in which platinum metals are in the form of a cation or cationic complex, e.g., $Pt(NH_3)_6Cl_4$ is particularly useful.

ZSM-5, when employed as a ctalyst, should be dehydrated at least partially. This can be done by heating to a temperature in the range of 200° to 600° C. in an inert atmosphere, such as air, nitrogen, etc. and at atmospheric or subatmospheric pressures for between land 48 hours. Dehydration can also be performed at lower temperatures merely by placing the ZSM-5 catalyst in a vacuum, but a longer time is required to obtain a sufficient amount of dehydration.

Zeolite ZSM-5 can be suitably prepared by preparing a solution containing tetrapropyl ammonium hydroxide, sodium oxide, an alumina and silica source, and water and having a composition, in terms of mole ratios of oxides, falling within the following ranges:

TABLE C

|  | Broad | Preferred | Particularly Preferred |
|---|---|---|---|
| OH⁻/SiO₂ | 0.07 – 10 | 0.1 – 2.0 | 0.2 0 – 0.75 |
| R₄N+/(R₄N⁺+Na⁺) | 0.2 – 0.95 | 0.3 – 0.9 | 0.4 – 0.9 |
| H₂O/OH⁻ | 10 – 300 | 10 – 300 | 10 – 300 |
| SiO₂/Al₂O₃ | 5 – 100 | 10 – 60 | 10 – 40 | wherein R is propyl, and maintaining the mixture until crystals of the zeolite are formed. Thereafter, the crystals are separated from the liquid and recovered. Typical reaction conditions consist of heating the foregoing reaction mixture to a temperature of from about 100° C to 175° C. for a period of time of from about six hours to sixty days. A more preferred temperature range is from about 150° to 175° C. with the amount of time at a temperature in such range being from about 12 hours to 8 days.

The digestion of the gel particles is carried out until crystals form. The solid product is separated from the reaction medium, as by cooling the whole to room temperature, filtering, and water washing.

The foregoing product is dried, e.g. at 230° F., for from about 8 hours to 24 hours. Of course, milder conditions may be employed if desired, e.g., room temperature under vacuum.

ZSM-5 can be prepared utilizing materials which supply the appropriate oxide. Such compositions include for an aluminosilicate, sodium aluminate, alumina, sodium silicate, silica hydroxol, silica gel, silicic acid, sodium hydroxide and tetrapropylammonium hydroxide. It will be understood that each oxide component utilized in the reaction mixture for preparing a member of the ZSM-5 family can be supplied by one or more initial reactants and they can be mixed together in any order. For example, sodium oxide can be supplied by an aqueous solution of sodium hydroxide or by an aqueous solution of sodium silicate; tetrapropylammonium cation can be supplied by the bromide salt. The reaction mixture can be prepared either batchwise or continuously. Crystal size and crystallization time of the ZSM-5 composition will vary with the nature of the reaction mixture employed. The form of catalyst ZSM-5 usable in the practice of the present invention is that in which the silica/alumina molar ratio is substantially greater than 10/1.

The crystalline aluminosilicate ZSM-5 per se forms no part of the present invention; it is only the use of ZSM-5 in the processes of the present invention that is herein claimed.

EXAMPLE 1

Preparation of H-ZSM-5 (42.6/1 silica to alumina ratio)

3.19 gm. $NaAlO_2$ were dissolved in 99 ml of a 2.37 NTPA-OH (tetrapropyl ammonium hydroxide) solution and 9 ml. hot water. To this was added 76.3 Ludox and mixed until a smooth, creamy gel formed. The gel was placed in a pyrex liner in an autoclave, run five days at 175° C., cooled, removed and washed with one liter of water. The product was dilatent and mainly crystalline with crystal sizes of less than one micron. The product was dried at 230° F. and calcined for 10 hours at 1000° F. in air. The product was identified by X-ray analysis as ZSM-5. The physical properties are given below:

| | |
|---|---|
| Wt. % $SiO_2$ | 94.6 |
| Wt. % $Al_2O_3$ | 3.8 |
| Wt. % Na | 1.44 |
| $SiO_2/A_2O_3$ | 42.3 |
| Wt. % $H_2O$ | 6.50 |
| n-hexane adsorption | 10.5 |
| cyclohexane adsorption | 5.07 |
| $m^2/g$ | 230 |
| crystallinity | 80% |

An exchange product was also prepared by reacting the above-described product with ammonium chloride. In this exchange the sodium ions present were exchanged by ammonium ions. The silica/alumina ratio of the exchange product was also 42.3/1. The exchange product was prepared by treating ZSM-5 with a saturated $NH_4Cl$ solution for 5 hours at room temperature with stirring. The product was filtered and a fresh solution of 25 wt % $NH_4Cl$ was added and reacted for 16 hours at 100° C., filtered, and again reacted with fresh solution of 25 wt % $NH_4Cl$, water washed to remove all chloride ions and dried at 230° F.

EXAMPLE 2

Reaction of 1-Decene and Phenol Over H-ZSM-5 (42.6/1)

A mixture of phenol (19 gm) and 1-decene (28.2 gm) was stirred for 1 ½ hours at 182° C. in the liquid phase with 1/12 its weight of the H-ZSM-5 catalyst of example 1. The catalyst had previously been calcined for 2 hours in air at 900° F. The reaction was terminated, the catalyst filtered off and the reaction products examined by gas chromatography and spectroscopy. About 1% conversion of reactants to alkylate was observed.

EXAMPLE 3

Preparation of Zeolite H-ZSM-5 (17/1 Silica to alumina ratio)

In the preparation of this catalyst the quaternary ammonium aluminosilicate was synthesized first by the following process which involved recycling the supernatant liquor from a previous preparation.

The initial preparation consisted of reacting the following solutions:

Solution A
  15.6 g. NaOH (97.3 st.% NaOH)
  1200 cc $H_2O$
  374.0 g. TPABr (tetra propyl ammonium bromide)
Solution B
  19.2 g. $NaAlO_2$ (44.5 wt.% $Al_2O_3$, 31.6 wt.% $Na_2O$
  1200 cc $H_2O$
Solution C
  460 g. Ludox 30 wt.% $SiO_2$ These solutions were mixed in the following order: solution B added to solution A, finally solution C (Ludox) was added to this mixture and stirred for 15 minutes and charged to a stirred autoclave. Stirring was continued during the run. The reaction was allowed to continue for 70 hours at a temperature of 249° to 309° F and at a pressure of 18 to 65 psig until crystallization of the ZSM-5 product was obtained. The product was separated from the supernatant solution by filtration and washing. This solution was then reused for the preparation of the Na TPA ZSM-5 used in instant catalyst.

In preparing the particular Na TPA ZSM-5 of this example, 2840 grams of the mother liquor separated from product ZSM-5 above was used. To this was added depleted components: 13.6 g. NaOH (97.3 wt.% NaOH), 16.8 g. $NaAlO_2$ (44.5 wt. % $Al_2O_3$, 31.6 wt. % $Na_2O$) and silica as 120 g. Cab-O-Sil (100% $SiO_2$) as fine powder. These components were charged to a stirred autoclave, held for 90 hours at 282°–298° F under a 52 to 61 psig pressure. The resulting Na TPA ZSM-5 product was separated from the liquor by filtration and washing.

The composition of the product at this point was:

| | |
|---|---|
| Na, wt. % | 1.5 |
| $Al_2O_3$, wt. % | 8.8 |
| $SiO_2$, wt. % | 88.8 |
| $SiO_2/Al_2O_3$ | molar ratio of 17.2 |

The product by X-ray analysis was 85% crystalline when compared to an established standard.

In preparing the instant acid ZSM-5 form 105 g. of the above Na TPA ZSM-5 was contacted 7 times, 5 one hour and 2 overnight, with a 5 wt.% $NH_4Cl$ solution at room temperature, followed by water washing until the effluent water was essentially free of residual chloride. The water washed product was air dried at 230° F and calcined for 10 hours at 1000° F.

The final product had a residual sodium content of 0.48 wt.%.

This calcined product was used in the subsequent conversion process.

EXAMPLE 4

Preparation of Zeolite H-ZSM-5 (37/1 Silica to alumina ratio)

The ZSM-5 crystalline aluminosilicate used in preparing this catalyst was synthesized by reacting the following solutions:

Solution A
 0.56 lbs. NaAlO$_2$ (44.7 wt.% Al$_2$O$_3$, wl. 6 wt.% Na$_2$O)
 14.0 lbs. Water
Solution B
 44.7 lbs. Q-Brand Silicate (28.9 wt.% SiO$_2$, 8.9 wt.% Na$_2$O)
 56.0 lbs. Water
Solution C
 5.6 lbs. TPABr (tetra propyl ammonium bromide)
 28.0 lbs. Water
Solution D
 4.47 lbs. H$_2$SO$_4$
 14.0 lbs. Water These solutions were intermixed in the following order: solution C added into solution B, then solution A added to this combination and finally solution D was added. This mixture, a firm gel type slurry, was further mixed until a thick slurry resulted. This slurry was held at a temperature of 180°–212° F with steam heated submerged heating coils for 167 hours at atmospheric pressure until the crystalline product of adequate crystallinity was formed. The resulting product was separated from the supernatant liquor by filtration and washing.

The composition of the final product on dry basis was:

| | |
|---|---|
| Na, wt. % | 0.8 |
| N, wt. % | 0.52 |
| Al$_2$O$_3$, wt. % | 4.4 |
| SiO$_2$, wt. % | 96.8 |
| SiO$_2$/Al$_2$O$_3$ | molar ratio 37/1 |

X-ray analysis showed this product to be 90% crystalline when compared to an established standard.

In preparing the acid ZSM-5 form of this example, a quantity of the above Na TPA ZSM-5 was first dried at 230° F and then calcined for 10 hours at 1000° F to remove the TPA ion by oxidation prior to ion exchange with NH$_4$Cl to reduce the residual sodium content.

The ion exchange process involved contacting 939 g. of the calcined Na ZSM-5 with a 10 wt.% NH$_4$Cl solution for three one hour and one overnight contacts at room temperature with stirring. In each contact 2.07 lbs. NH$_4$Cl was dissolved in 19.7 lbs.water. After the fourth contact the product was washed essentially free of chloride ion, and dried at 230° F. A part of this batch was calcined for 10 hours at 1000° F and used in the catalysis of the polar compounds.

The residual sodium of the final calcined catalyst was 0.02 wt.% Na.

The following representative reactions, involving the conversion of at least one polar organic oxygenate over a ZSM-5 zeolite, were carried out in sealed glass vessels as opposed to flow systems. Each reaction was carried out in the same fashion. Reactants and zeolites were charged into a glass ampoule and heated at autogenous pressure for 3 hours at 200°–250° C. The tubes were opened, approximate conversions determined by gas, liquid chromatography and the major reaction product(s) isolated by preparative gas, liquid chromatography and identified by infrared comparison to an authetic sample.

EXAMPLE 5

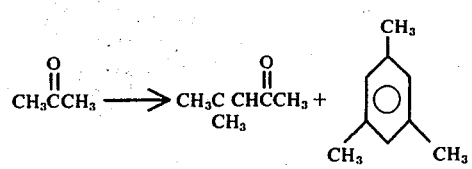

catalyst: H-ZSM-5 of example 3 (silica/alumina: 17/1)

Amounts:
 Catalyst  1 g
 CH$_3$CCH$_3$ (ketone)  10 g
 Conversion: 25%

Other data:
6.5 grams of unreacted acetone was removed by distillation leaving a 3.5 residue which contained 1 gram of acetone, a mixture of mesityl oxide and mesitylene in a 9 to 1 ratio.

EXAMPLE 6

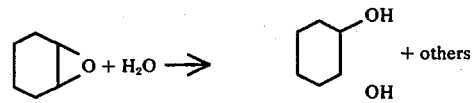

Catalyst: H-ZSM-5 of example 4 (silica/alumina: 37/1)

Amounts:
 Catalyst  1 g
 (epoxide)  10 g
 H$_2$O  1 g
 conversion:  90% other data:
The catalyst was removed by filtration, yielding 4 grams of crude trans-1, 2-cyclohexanediol.

EXAMPLE 7

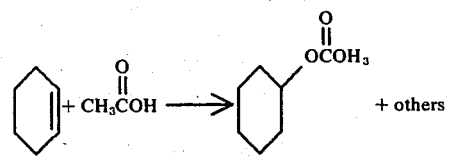

Catalyst: H-ZSM-5 of example 3 (silica/alumina: 17/1)

Amounts:
 catalyst  .2 g
 (benzene)  8.0 g
 CH$_3$C OH (acetic acid)  1.0 g
 conversion:  60% other data:

5.1 gram of unreacted starting material was removed by distillation. Cyclohexyl acetate was shown to be the major component in the high boiling residue.

Other reactions which are more efficiently converted by the catalysts of the present invention include by way of further example the following:

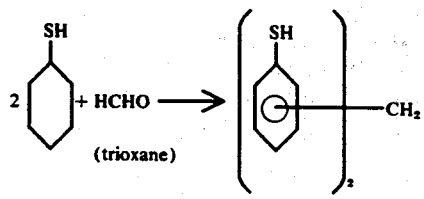

EXAMPLE 8

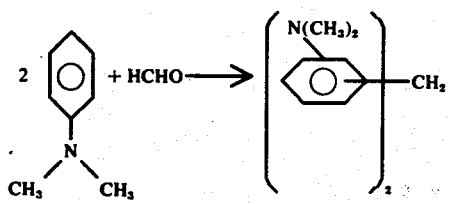

EXAMPLE 9

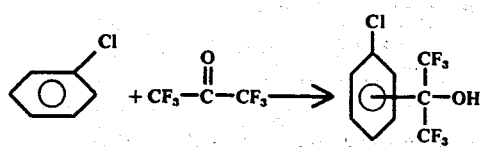

EXAMPLE 10

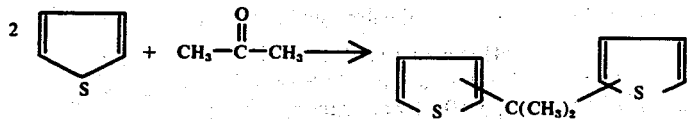

EXAMPLE 11

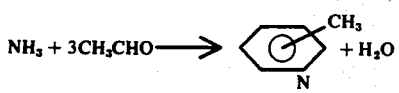

EXAMPLE 12

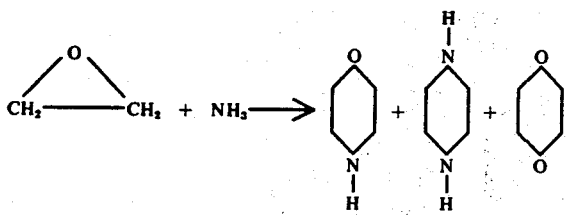

EXAMPLE 13

Preparation of high silica to alumina ratio zeolite y by chelation

The catalyst used in examples 14–15 was a chelated rare earth zeolite Y (REYO having a silica/alumina ratio of 19.5/1. A high silica Y faujasite was synthesized by the procedure set forth in Belgium Pat. No. 598,582. Preparational details of this synthesis were as follows:

Solution A

Caustic Aluminate Solution
900 g. $NaAlO_2$ (Nalco 44.5% $Al_2O_3$, 33.5 $Na_2O$
534 g. NaOH 77.5 wt.% $Na_2O$
2832 cc. $H_2O$ Solution B 7344 g. (6108 cc) Ludox LS 30 wt.% $SiO_2$ Solution B was added to freshly prepared warm solution A while being stirred vigorously. Stirring was continued for an additional 30 minute period after addition. The resulting slurry was split into three four-liter battery jars and allowed to age at room temperature for 20–24 hours. Following the room aging the containers were covered and placed in a hot water bath at 200° F and held for 192 hours until a crystalline faujasite product was formed. At this point, the crystalline product was separated from the supernatant liquid by filtration and washing.

The composition of the sodium Y as prepared by the procedure above was Na, wt.% 8.6, $Al_2O_3$, wt.% 19.0, $SiO_2$, wt.% 68.7, X-ray analysis showed the product to be 75% crystalline.

225 g. of the above dry NaY catalyst was contacted four times for 24 hours each at 200° F. with 20 g. EDTA (ethylene diamine tetra acetic acid) and 200 cc water to reduce alumina content by chelation. After each contact the filter cake was washed with 200 cc. of water.

Following the EDTA treatment, which reduces the alumina content, the dealuminized faujasite was ion exchanged with a continuous flow of 90 lbs. of solution containing 5 wt.% $RECl_3.6H_2O$ + 2 wt.%$NH_4Cl$ over a 24 period followed by water washing until the effluent was essentially free of soluble chloride ion.

The exchanged faujasite was dired at 230° F, pelleted and sized 4 to 10 mesh Tyler, calcined for 10 hours at 1000° F followed by steam treatment at 1200° F for 72 hours with steam at 15 psig.

Composition of the rare earth exchanged catalyst was $(RE)_2O_3$, wt.% 6.7, $Al_2O_3$, wt.% 7.4, $SiO_2$, wt.% 84.6, Na, wt.% 0.24, $SiO_2/Al_2O_3$ molar ratio of 19.5.

EXAMPLE 14

Condensation of phenol with formaldehyde over high silica to alumina ratio, Chelated, REY (19.5/1)

Sixty-four grams of phenol and 5 grams of the finely-powdered catalyst of example 13 (previously calcined for 3 hours at 500° F. in a helium flow) were heated with stirring to the reaction temperature (i.e., about 182° C.). A solution containing 6.6 grams of trioxane, the crystalline trimer of formaldehyde, in 50 cc of benzene solvent, was introduced through a long stainless steel needle inserted well below the surface of the reaction mixture. The trioxane solution was metered into the needle by a motor-driven syringe pump over a period of about 1.75 hours. The reaction was terminated and gas chromatographic examination of the reaction mixture was effected. About 1.9 wt.% of higher boiling products were observed whose retention times corresponded to the expected bisphenol products, $C_{13}H_{12}O_2$.

EXAMPLE 15

Reaction of 1-Decene and Phenol over high silica to alumina ratio, Chelated REY (19.5/1)

A mixture of phenol (60 gm) and 1-decene (28.2gm) was stirred for 1½ hours at 182° C. in the liquid phase with 3.0 grams of the catalyst of example 13. The catalyst had previously been calcined for 3 hours in helium 500° F. The reaction was terminated, the catalyst filtered off, and the reaction products examined by gas chromatography and spectroscopy. About 2.2% conversion of reactants to products whose retention times corresponded to monoalkylate was observed.

EXAMPLE 16

Preparation of high silica to alumina ratio Zeolite Beta (23.3/1)

4.4 grams of sodium aluminate (made by reacting 41.8 wt % $Al_2O_3$ with 31.3 wt % $Na_2O$) was added to 41.6 grams of a 40% aqueous solution of tetraethylammonium hydroxide and 109 grams of Ludox (containing 30 wt % of $SiO_2$). The collodial silica was added last. The mixture was vigorously agitated for ten minutes. The constituents were then added to a sealed autoclave and heated to and held at 300° F. for 4-6 days, generating a pressure of 190 to 400 psig. The final product was separated by filtration followed by water washing and drying at 230° F.

The typical analysis of the beta aluminosilicate product was: sodium, 0.37 wt %; $Al_2O_3$, 7.1 wt %; $SiO_2$, 93.2 wt %. The adsorptive properties of the product were as follows:

|  | Wt. % |
|---|---|
| cyclohexane | 10–20 |
| n-hexane | 10–17 |
| water | 15 |

32.2 gram of oven dried material prepared as described above was contacted four times with 5 wt % of $NH_4Cl$ solution for three one-hour contacts and one overnight contact at 190° F. The crystalline aluminosilicate was separated from the contacting solution after each contact by filtration. After final contact the sample was water washed and then dried at 230° F., followed by calcination at 1000° F. for ten hours.

The final chemical and physical properties of the product were as follows:

|  | Wt. % |
|---|---|
| Na | 0.05 |
| $Al_2O_3$ | 6.63 |
| $SiO_2$ | 91.0 |

(silica/alumina molar ratio = 23.3)

The adsorptive properties of the product were as follows:

|  | Wt. % |
|---|---|
| Cyclohexane | 19.3 |
| n-hexane | 17.4 |
| water | 11.3 |

The final surface area of the catalyst was 575 meters$^2$/gram.

EXAMPLE 17

Preparation of high silica to alumina ratio Dealuminized Mordenite (39.2/1)

H-mordenite (Norton Co., Code B6-10) was steamed for 2 hours at 1000° F., then extracted continuously with 50 cc per gram of catalyst of 1.0 NHCl at 180° F. over a 16 hour period, water washed until the extract was chloride ion-free and dried overnight in a 110° C. oven. The cycle was repeated 12 times. Following is an analysis of the product:

|  | Fresh | After 1st Cycle | After 12th Cycle |
|---|---|---|---|
| $SiO_2$, wt % | — | 91.7 | 94.2 |
| $Al_2O_3$, wt % | — | 7.6 | 4.08 |
| $SiO_2/Al_2O_3$ | 11.0 | 20.5 | 39.2 |
| Adsorption, wt % |  |  |  |
| $H_2O$ | — | 8.4 | 2.2 |
| n-$C_6$ | — | 5.5 | 3.9 |
| Cy-$C_6$ | — | 6.7 | 5.7 |

EXAMPLE 18

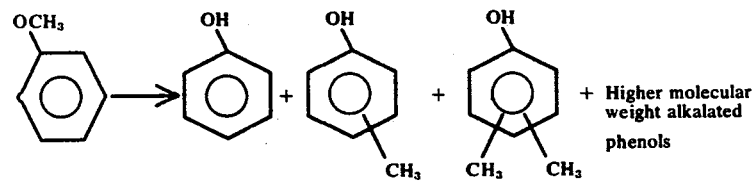

+ Higher molecular weight alkalated phenols catalyst:-catalyst beta of example 16 (silica/alumina: 23.3/1).

amounts: catalyst beta .5 g
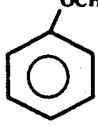 10 g conversion: approximately 100%

EXAMPLE 19

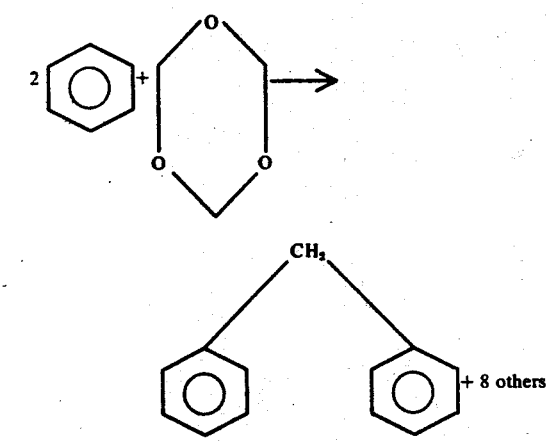

-continued
catalyst: beta of example 16 .1 g

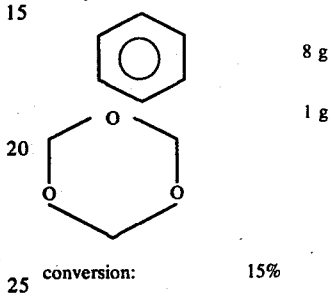  8 g 1 g conversion: 15% other data:
 6 grams of benzene and trioxane were removed. The remaining material was composed of nine products, 41% of which was diphenylmethane.

EXAMPLE 20

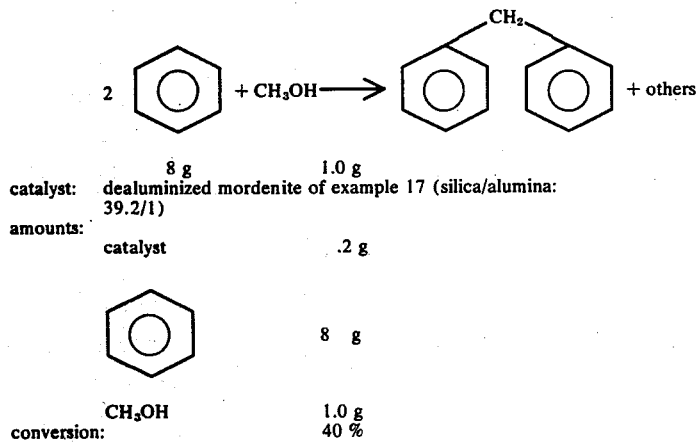

|  | 8 g | 1.0 g |
| --- | --- | --- | catalyst: dealuminized mordenite of example 17 (silica/alumina: 39.2/1)
amounts:
 catalyst .2 g
 benzene 8 g
 CH₃OH 1.0 g
conversion: 40 % other data:
 7.2 grams of unreacted benzene and methanol were removed leaving 0.3 grams of high boiling material of which most was diphenylmethane.

EXAMPLE 21

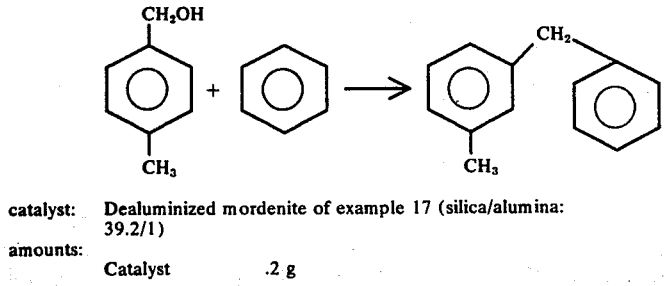

catalyst: Dealuminized mordenite of example 17 (silica/alumina: 39.2/1)
amounts:
 Catalyst .2 g

EXAMPLE 21 -continued

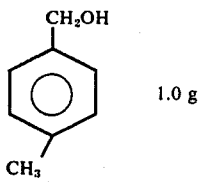 1.0 g

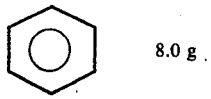 8.0 g conversion: 100 % other data:

Excess benzene was removed and the residue distilled, yielding 1.0 g of p-methyldiphenylmethane with a b.p. of 130°–133° C. at 3 mm.

EXAMPLE 22

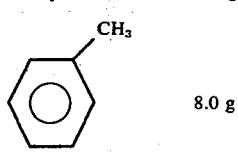

catalyst: Dealuminized mordenite of example 17 (silica/alumina: 39.2/1)
amounts:
catalyst   .2 g

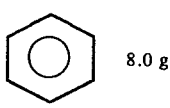 8.0 g

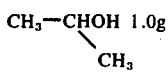 1.0g conversion:   90 % other data:

The catalyst was removed to yield 6.2 gram of unreacted benzene and isopropanol. Examination of the high boiling residue showed it to contain cumene as a major product with a small amount of p-disopropylbenzene and a trace of odisopropylbenzene.

EXAMPLE 23

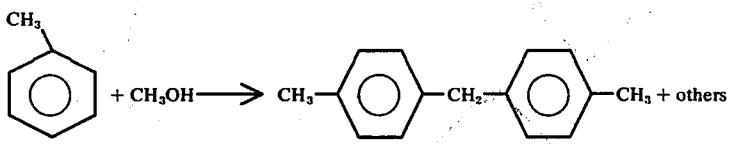

catalyst: Dealuminized mordenite of Example 17 (silica/alumina: 39.2/1)
amounts:
Catalyst   .2 g

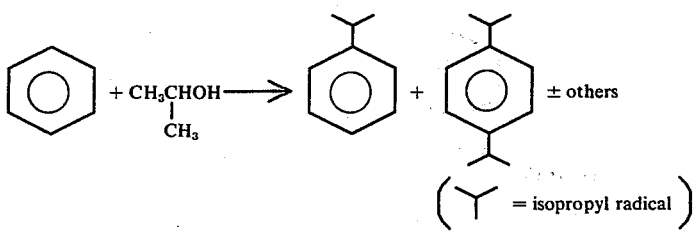

conversion:   40% other data:

6.9 grams of unreacted toluene and methanol were removed, yielding as a major product in the complex residue p-ditolylmethane.

EXAMPLE 24

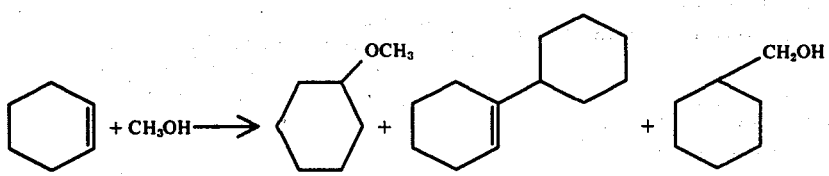

catalyst: Dealuminized mordenite of example 17 (silica/alumina: 39.2/1)
amounts:
    catalyst      2.g
          8.g
    CH$_3$OH      1.g
conversion:      50 % other data:

4.7 gram of unreacted cyclohexene and methanol were removed. The remaining residue contained cyclohexyl methyl ether and cyclohexylcyclohexane in a 1/1 ratio.

Other reactions which are more efficiently converted by the catalysts of the present invention include by way of further example the following:

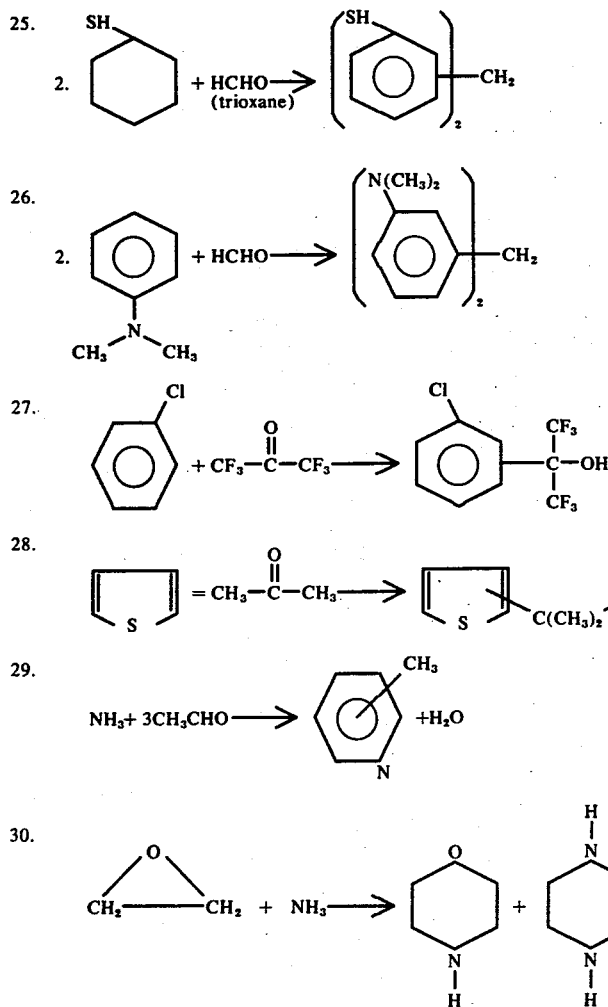

silica/alumina ratios greater than 10 has been set forth. It is to be understood, however, that the practice of the present invention is also applicable to isomorphs of said crystalline aluminosilicates. For example, the aluminum may be replaced by elements such as gallium and silicon by elements such as germanium.

The invention may be embodied in other specific forms without departing from the spirit or essential characteristics thereof. The present embodiments are therefore to be considered in all respects as illustrative and not restrictive, the scope of the invention being In the foregoing portions of the specification, a novel process for converting polar organic compounds by means of crystalline aluminosilicate catalysts with

What is claimed is:

1. In the process of dehydrating an alcohol, by contacting it at a temperature of about 70° to 1400° F with a solid crystalline aluminosilicate zeolite acidic catalyst having a pore size sufficient to permit the diffusion of said alcohol thereinto and to permit dehydration therein, the improvement whereby carrying out said dehydration with exceptional catalyst stability, which comprises utilizing said zeolite having a silica to alumina ratio substantially greater than 10 to 1.

2. The process claimed in claim 1 wherein said alcohol contains up to about 6 carbon atoms.

* * * * *

UNITED STATES PATENT AND TRADEMARK OFFICE
CERTIFICATE OF CORRECTION

PATENT NO. : 4,011,278
DATED : March 8, 1977
INVENTOR(S) : CHARLES J. PLANK, EDWARD J. KOSINSKI and GEORGE T. KERR It is certified that error appears in the above-identified patent and that said Letters Patent are hereby corrected as shown below:

Column 1, line 24    "cavaties" should be --cavities--.

Column 1, line 43    After "$Na_2$" should be --$K_2$--.

Column 3, line 41    "spectromete" should be --spectrometer--.

Column 4, line 18    "ctalyst" should be --catalyst--.

Column 4, line 22    "land" should be --la dn--.

Column 5, line 37    "$SiO_2/A_2O_3$" should be --$SiO_2/Al_2O_3$

Signed and Sealed this

Twenty-seventh Day of September 1977

[SEAL]

Attest:

RUTH C. MASON
*Attesting Officer*

LUTRELLE F. PARKER
*Acting Commissioner of Patents and Trademarks*